United States Patent
Govari et al.

(10) Patent No.: US 12,290,306 B2
(45) Date of Patent: May 6, 2025

(54) USING UNIPOLAR CONFIGURATION FOR IRREVERSIBLE-ELECTROPORATION (IRE)

(71) Applicant: BIOSENSE WEBSTER (ISRAEL) LTD., Yokneam (IL)

(72) Inventors: Assaf Govari, Haifa (IL); Andres Claudio Altmann, Haifa (IL); Yuri Shamis, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 716 days.

(21) Appl. No.: 17/073,467

(22) Filed: Oct. 19, 2020

(65) Prior Publication Data

US 2022/0117655 A1    Apr. 21, 2022

(51) Int. Cl.
*A61B 18/14*      (2006.01)
*A61B 18/12*      (2006.01)
*A61B 18/00*      (2006.01)

(52) U.S. Cl.
CPC ...... *A61B 18/1492* (2013.01); *A61B 18/1206* (2013.01); *A61B 2018/00178* (2013.01); *A61B 2018/00214* (2013.01); *A61B 2018/00351* (2013.01); *A61B 2018/00577* (2013.01); *A61B 2018/00613* (2013.01);
(Continued)

(58) Field of Classification Search
CPC ............ A61B 18/1492; A61B 18/1206; A61B 2018/00178; A61B 2018/00214; A61B 2018/00351; A61B 2018/00577; A61B 2018/00613; A61B 2018/124; A61B 2018/1253; A61B 2018/1266; A61B 2018/1467
See application file for complete search history.

(56) References Cited

U.S. PATENT DOCUMENTS 7,048,734 B1 *   5/2006   Fleischman ....... A61M 25/0147
                                                           606/41
8,048,067 B2    11/2011   Davalos
(Continued)

FOREIGN PATENT DOCUMENTS

CN          111248994 A      6/2020
EP           3399933 A1     11/2018
(Continued)

OTHER PUBLICATIONS

European Search Report for corresponding EPA No. 21165804.2 dated Sep. 21, 2021.

*Primary Examiner* — Sean W Collins

(57) ABSTRACT

A pulsed field ablation (PFA) system includes a composite electrode, a body-surface electrode, a PFA generator, and a processor. The composite electrode is coupled to a distal end of a catheter configured for insertion into an organ of a patient. The body-surface electrode is configured to be attached to a skin of the patient. The PFA generator is configured to be electrically connected to the composite electrode of the catheter and to the body-surface electrode, and to generate Direct-Current (DC) PFA pulses. The processor is configured to control the PFA generator to apply the DC PFA pulses between the composite electrode and the body-surface electrode while the composite electrode is placed in contact with target tissue of the organ and the body-surface electrode is in contact with the skin of the patient.

13 Claims, 3 Drawing Sheets

(52) U.S. Cl.
CPC . *A61B 2018/124* (2013.01); *A61B 2018/1253* (2013.01); *A61B 2018/1266* (2013.01); *A61B 2018/1467* (2013.01)

(56) References Cited

U.S. PATENT DOCUMENTS

| | | | |
|---|---|---|---|
| 8,221,411 B2 | 7/2012 | Francischelli | |
| 8,295,902 B2 | 10/2012 | Salahieh | |
| 10,271,893 B2 | 4/2019 | Stewart | |
| 10,342,598 B2 | 7/2019 | Long | |
| 10,531,914 B2 | 1/2020 | Stewart | |
| 2009/0131993 A1* | 5/2009 | Rousso | A61N 1/36017 607/2 |
| 2010/0261994 A1 | 10/2010 | Davalos | |
| 2011/0160514 A1 | 6/2011 | Long | |
| 2013/0296679 A1* | 11/2013 | Condie | A61B 5/6856 600/374 |
| 2014/0018880 A1 | 1/2014 | Zarins | |
| 2014/0276755 A1* | 9/2014 | Cao | A61N 5/00 607/101 |
| 2016/0051324 A1 | 2/2016 | Stewart | |
| 2016/0166310 A1 | 6/2016 | Stewart | |
| 2018/0085160 A1* | 3/2018 | Viswanathan | A61N 1/371 |
| 2018/0289417 A1 | 10/2018 | Schweitzer | |
| 2019/0030328 A1* | 1/2019 | Stewart | A61B 18/1492 |
| 2019/0223948 A1 | 7/2019 | Stewart | |
| 2019/0307500 A1* | 10/2019 | Byrd | A61B 34/20 |
| 2020/0069364 A1 | 3/2020 | Salahieh | |
| 2020/0107879 A1 | 4/2020 | Stewart | |
| 2021/0228260 A1* | 7/2021 | Canady, Jr. | A61B 18/1206 |

FOREIGN PATENT DOCUMENTS

| | | |
|---|---|---|
| EP | 3576657 A1 | 12/2019 |
| EP | 3578124 A1 | 12/2019 |
| RU | 2008133567 A | 2/2010 |

* cited by examiner

USING UNIPOLAR CONFIGURATION FOR IRREVERSIBLE-ELECTROPORATION (IRE)

FIELD OF THE INVENTION

The present invention relates generally to invasive ablation, and particularly to irreversible electroporation (IRE) of cardiac tissue in unipolar mode.

BACKGROUND OF THE INVENTION

Using a multi-electrode catheter for irreversible electroporation (IRE) has been previously proposed in the patent literature. For example, PCT International Publication WO 2018/191149 describes electroporation systems and methods of energizing a catheter for delivering electroporation. A catheter for delivering electroporation includes a distal section and an electrode assembly. The distal section is configured to be positioned in a vein within a body. The vein defines a central axis. The electrode assembly is coupled to the distal section and includes a structure and a plurality of electrodes distributed thereabout. The structure is configured to at least partially contact the vein. Each of the electrodes is configured to be selectively energized to form a circumferential ring of energized electrodes that is concentric with the central axis of the vein. In an embodiment, each electrode is individually wired such that it can be selectively paired or combined with any other electrode to act as a bipolar or a multi-polar electrode.

As another example, U.S. Pat. No. 8,295,902 describes a tissue electrode assembly that includes a membrane configured to form an expandable, conformable body that is deployable in a patient. The assembly further includes a flexible circuit positioned on a surface of the membrane. An electrically-conductive electrode covers at least a portion of the flexible circuit and a portion of the surface of the membrane not covered by the flexible circuit, wherein the electrically-conductive electrode is foldable upon itself with the membrane to a delivery conformation having a diameter suitable for minimally-invasive delivery of the assembly to the patient. In an embodiment, a pattern of multiple electrodes deposited on the membrane can collectively create a large electrode array of energy-transmitting elements.

SUMMARY OF THE INVENTION

An embodiment of the present invention that is described hereinafter provides a pulsed field ablation (PFA) system including a composite electrode, a body-surface electrode, a PFA generator, and a processor. The composite electrode is coupled to a distal end of a catheter configured for insertion into an organ of a patient. The body-surface electrode is configured to be attached to a skin of the patient. The PFA generator is configured to be electrically connected to the composite electrode of the catheter and to the body-surface electrode, and to generate Direct-Current (DC) PFA pulses. The processor is configured to control the PFA generator to apply the DC PFA pulses between the composite electrode and the body-surface electrode while the composite electrode is placed in contact with target tissue of the organ and the body-surface electrode is in contact with the skin of the patient.

In some embodiments, the catheter includes multiple electrodes, and includes a switching assembly that is configured to electrically short the multiple electrodes to one another to form the composite electrode.

In some embodiments, the catheter includes an expandable frame coupled to the distal end of the catheter, with the multiple electrodes disposed on the expandable frame.

In an embodiment, the catheter is a tip catheter having a tip electrode that is used as the composite electrode.

In another embodiment, the catheter includes multiple electrodes that are permanently short circuited to one another by electrical connections disposed on the catheter, to form the composite electrode.

In some embodiments, the PFA generator is configured to generate the DC PFA pulses with voltage polarities that alternate from pulse to pulse.

In other embodiments, the PFA generator is configured to generate the DC PFA pulses in multiple bursts separated by pause intervals.

In an embodiment, the DC PFA pulses are dual-polarity DC PFA pulses.

There is additionally provided, in accordance with another embodiment of the present invention, a pulsed field ablation (PFA) method including inserting into an organ of a patient a composite electrode that is coupled to a distal end of a catheter. A body-surface electrode is attached to a skin of the patient. Direct-Current (DC) PFA pulses are applied between the composite electrode of the catheter and the body-surface electrode while the composite electrode is placed in contact with target tissue of the organ and the body-surface electrode is in contact with the skin of the patient.

BRIEF DESCRIPTION OF THE DRAWINGS

The present invention will be more fully understood from the following detailed description of the embodiments thereof, taken together with the drawings in which.

DETAILED DESCRIPTION OF EMBODIMENTS

Overview

Figure 1:
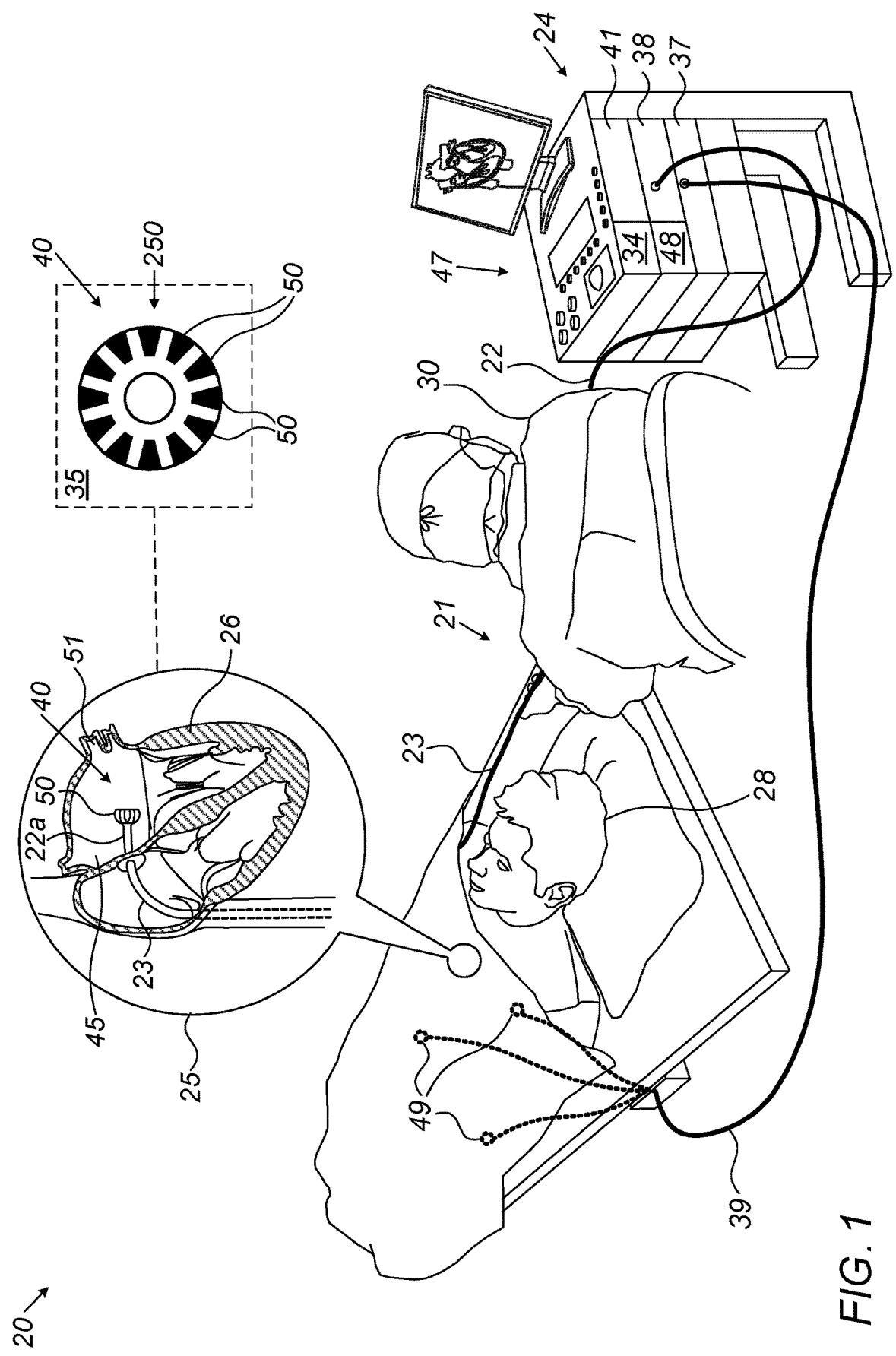
FIG. 1 is a schematic, pictorial illustration of a catheter-based irreversible electroporation (IRE) system, in accordance with an embodiment of the present invention.

Irreversible electroporation (IRE), also called Pulsed Field Ablation (PFA), may be used as an invasive therapeutic modality to kill tissue cells by subjecting them to high-voltage pulses. Specifically, IRE pulses have a potential use to kill myocardium tissue cells in order to treat cardiac arrhythmia. Cellular destruction occurs when the transmembrane potential exceeds a threshold, leading to cell death and thus the development of a tissue lesion. Therefore, of particular interest is the use of high-voltage bipolar electric pulses, e.g., using a selected pair of electrodes in contact with tissue, to generate high electric fields, e.g., above a certain threshold to kill tissue cells between the electrodes.

IRE is typically performed by applying high-voltage pulses between pairs of electrodes that are relatively close to each other, since the generated field strength must be high.

In other words, IRE is typically a bipolar operation, and is implemented over a relatively small region. However, if IRE is to be applied to a large tissue region, such as for ablating an entire circumference of an ostium of a pulmonary vein (PV) using bipolar pulses, the ablation must be repeatedly applied to multiple separate parts of the region, which is time consuming, and therefore may result in inconsistent results, due to, for example, cardiac motion that destabilizes catheter contact with the ostium.

Embodiments of the present invention that are described hereinafter use a multi-electrode catheter, such as a balloon, basket, or lasso catheter, and connect multiple (e.g., all) electrodes together to effectively form one composite catheter electrode. The catheter is inserted into a patient, and the composite electrode is connected to one lead of an output of a PFA generator. A body-surface electrode ("skin electrode"), such as a back patch, is used as a return electrode for the generator. Typically, the skin electrode is relatively large (e.g., 10 cm×20 cm). The PFA generator generates PFA pulses between the composite electrode of the catheter and the skin electrode, thereby performing IRE on the tissue contacted by the composite electrode. The PFA pulses are typically Direct-Current (DC) voltage pulses, e.g., rectangular voltage pulses. The parameter of the PFA pulses (e.g., pulse-width, duty cycle and amplitude) are typically chosen in accordance with a protocol that is proven to kill the intended target tissue with little or no damage to other tissue. In some embodiments, the PFA generator generates bursts of PFA pulses, wherein the pulses in each burst alternate in voltage polarity from one pulse to the next.

When applying PFA pulses using the disclosed technique, the current density near the composite electrode is higher than the current density at the external back patch due to the smaller surface area of the composite electrode versus that of the back patch. The higher current density causes the ablation to occur near the composite electrode and not near the back patch.

The multiple electrodes of the catheter may be connected in different ways to form the composite electrode. Connection may be formed, for example, using switching circuitry in a PFA generator. In another embodiment, the composite electrode is formed by using electrical connections at the distal end of the catheter, that form permanent short circuits between the electrodes disposed on the catheter.

In some embodiments, a catheter typically used in unipolar radiofrequency (RF) ablation, such as one having a single large electrode, e.g., a tip catheter having a tip electrode, can be used with the disclosed technique for unipolar PFA ablation. The sinusoidal RF ablation waveform has typically a maximal amplitude of 200 volts, and the RF energy destroys tissue by heating it. IRE/PFA pulses, on the other hand, are typically square waves DC pulses having voltage amplitudes above 500 V (1000 V peak to peak) and up to 2000 V, with an aim to achieve strong electric fields to kill tissue cells without a need for heat.

The disclosed technique typically uses protocols which are optimized to overcome muscle contraction, e.g., contraction of skeletal muscle, which is a side effect of DC unipolar IRE. To this end, the PFA pulses are generated with a high repetition rate (e.g., >100 KHz), with alternating voltage polarity that provides substantially zero DC average voltage.

For example, the PFA pulse may comprise a positive pulse and a negative pulse applied between the composite electrode and the patch, with pulse widths of 0.5-5 µs and a separation between the positive and negative pulses of 0.5-5 µs. The terms "positive" and "negative" used here refer to an arbitrarily chosen polarity between the two electrodes. The pulses may be grouped into pulse trains, each train comprising between two and a hundred DC PFA pulses, with a PFA pulse-to-PFA pulse period of 0.1-0.7 µs and interval between PFA pulse-trains between 10-100 µs. Such trains of pure ultrashort AC pulses ensure minimal muscle activation in the disclosed unipolar configuration.

By offering a unipolar PFA configuration as an alternative to bipolar PFA configuration, IRE ablation procedures, for example in an ostium of a PV using a catheter, can be made easier, while maintaining clinical efficacy.

System Description

FIG. 1 is a schematic, pictorial illustration of a catheter-based irreversible electroporation (IRE) system 20, in accordance with an embodiment of the present invention. System 20 comprises a catheter 21, wherein a shaft 22 of the catheter is inserted by a physician 30 through the vascular system of a patient 28 through a sheath 23. The physician then navigates a distal end 22a of shaft 22 to a target location inside a heart 26 of the patient 28 (inset 25).

Once distal end 22a of shaft 22 has reached the target location, physician 30 retracts sheath 23 and expands balloon 40, typically by pumping saline into balloon 40. Physician 30 then manipulates shaft 22 such that electrodes 50 disposed on the balloon 40 catheter engage an interior wall of a PV ostium 51 to apply high-voltage PFA pulses via electrodes 50 to ostium 51 tissue.

As seen in inset 25, distal end 22a is fitted with an expandable balloon 40 comprising multiple equidistant IRE electrodes 50. Due to the flattened shape of the distal portion of balloon 40, the distance between adjacent electrodes 50 remains approximately constant even where electrodes 50 cover the distal portion. Balloon 40 configuration therefore allows more effective electroporation (e.g., with approximately uniform electric field strength) between adjacent electrodes 50.

Certain aspects of inflatable balloons are addressed, for example, in U.S. patent application Ser. No. 16/993,092, filed Aug. 13, 2020, titled "Applying Bipolar Ablation Energy Between Shorted Electrode Groups," which is assigned to the assignee of the present patent application and whose disclosures are incorporated herein by reference.

In the embodiment described herein, catheter 21 may be used for any suitable diagnostic and/or therapeutic purpose, such as electrophysiological sensing and/or the aforementioned IRE isolation of PV ostium 51 tissue in left atrium 45 of heart 26.

The proximal end of catheter 21 is connected to switching assembly 48 comprised in console 24, with circuitry creating an effective composite electrode 250 by short-circuiting electrodes 50 one to the other, e.g., using switches of assembly 48. Electrodes 50 are connected to assembly 48 PFA by electrical wiring (shown in FIG. 2) running in shaft 22 of catheter 21. Console 24 further comprises a PFA pulse generator 38, to which assembly 48 is connected, where generator 38 is configured to apply the PFA pulses between composite electrode 250 and a skin patch electrode (shown in FIG. 2). An IRE pulse generator similar to PFA pulse generator 38 is described in U.S. patent application Ser. No. 16/701,989, filed Dec. 3, 2019, titled "Pulse Generator for Irreversible Electroporation," which is assigned to the assignee of the present patent application and whose disclosure is incorporated herein by reference.

Figure 2:
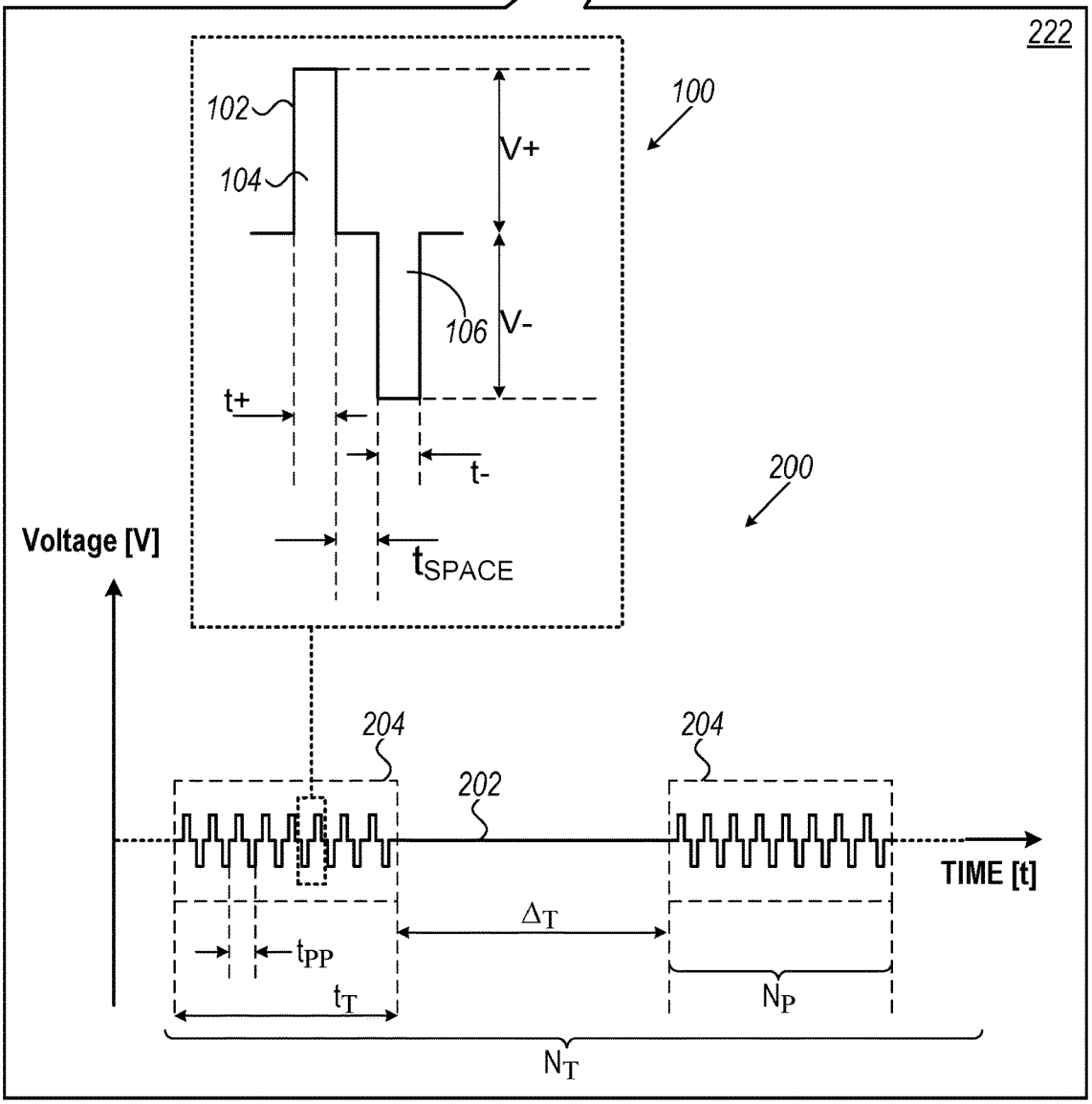
FIG. 2 is a schematic, pictorial illustration of the IRE catheter of FIG. 1 ablating an ostium of a pulmonary vein (PV) with bursts of unipolar pulsed field ablation (PFA) pulses, in accordance with an embodiment of the present invention.

A memory 34 of console 24 stores IRE protocols comprising PFA pulse parameters, such as peak-to-peak voltage and pulse width, as described in FIG. 2.

Console 24 comprises a processor 41, typically a general-purpose computer, with suitable front end and interface circuits 37 for receiving signals from catheter 21 and from external electrodes 49, which are typically placed around the chest of patient 28. For this purpose, processor 41 is connected to external electrodes 49 by wires running through a cable 39.

During a procedure, system 20 can track the respective locations of electrodes 50 inside heart 26 using the Active Current Location (ACL) method, provided by Biosense-Webster (Irvine, California), which is described in U.S. Pat. No. 8,456,182, whose disclosure is incorporated herein by reference.

In some embodiments, physician 30 can modify, from a user interface 47, any of the parameters of the unipolar IRE protocol used with composite electrode 250. User interface 47 may comprise any suitable type of input device, e.g., a keyboard, a mouse, or a trackball, among others.

Processor 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

In particular, processor 41 runs a dedicated protocol as disclosed herein, including in FIG. 3, which enables processor 41 to perform the disclosed steps, as further described below.

Using Unipolar Configuration for IRE

FIG. 2 is a schematic, pictorial illustration of irreversible electroporation (IRE) catheter 40 of FIG. 1 ablating ostium 51 of a pulmonary vein (PV) with pulse trains of unipolar pulsed-field ablation (PFA) pulses 100, in accordance with an embodiment of the present invention. FIG. 2 shows composite electrode 250 in contact with ostium over an entire circumference of the ostium. The composite electrode is connected via a cable 60 to switching assembly 48, where the separate wires of cable 60 that connect to electrodes 50 are short-circuited one with the other in assembly 48 to create effective composite electrode 250. A single conductor 62 connects switching assembly 48 to one end of PFA generator 38. The other lead of PFA generator 38 is connected to a back-patch electrode 66, attached to skin of the patient.

As noted above, implementing unipolar PFA using electrode 250 requires dedicated IRE protocols with suitable PFA pulses to be applied to the patient. In some embodiments, a provided PFA protocol divides (partitions) the PFA pulse delivery of a selected protocol into multiple pulse trains ("pulse bursts") 204 with pauses 202 between the pulse trains. The pauses permit muscle relaxation if any contraction occurs.

Inset 222 of FIG. 2 is a schematic illustration of a waveform 200 of PFA pulses, in accordance with an embodiment of the invention. In an IRE procedure, the PFA signals are delivered to electrodes 50 as waveform 200 having one or more pulse trains 204. Waveform 200 comprises $N_T$ pulse trains 204, wherein each train comprises $N_P$ dual-polarity DC pulses 100. The dual-polarity pulse shape is described below. The length of pulse train 204 is labeled as $t_T$. The period of dual-polarity pulses 100 within a pulse train 204 is labeled as $t_{PP}$, and the interval between consecutive trains 204 is labeled as $\Delta_T$, during which the signals are not applied. Typical values for the parameters of waveform 200 are given in Table 1 below.

A schematic illustration of a PFA pulse 100 is depicted in inset 222. As seen, a curve 102 depicts the voltage of PFA pulse 100 as a function of time in an PFA ablation procedure. The dual-polarity PFA pulse comprises a positive pulse 104 and a negative pulse 106, wherein the terms "positive" and "negative" refer to an arbitrarily chosen polarity of the electrodes 50 and 66 between which the PFA pulse is applied. The amplitude of positive pulse 104 is labeled as V+, and the temporal width of the DC pulse is labeled as t+. Similarly, the amplitude of negative pulse 106 is labeled as V−, and the temporal width of the DC pulse is labeled as t−. The temporal width between positive pulse 104 and negative pulse 106 is labeled as $t_{SPACE}$. Typical values for the parameters of dual-polarity pulse 100 are given in Table 1 below.

TABLE 1

Typical Values for the Parameters of Unipolar PFA Signals

| Parameter | Symbol | Typical Values |
|---|---|---|
| Pulse amplitudes | V+, V− | 500-2000 V |
| Pulse widths | t+, t− | 0.4-5 µs |
| Spacing between positive and negative pulse | $t_{SPACE}$ | 0.1-1 µs (1-10 ms when an optional radiofrequency (RF) signal is inserted between the positive and negative pulses) |
| Period of dual-polarity pulses in a pulse train | $t_{PP}$ | 1-12 µs |
| Length of pulse train | $t_T$ | <=100 µs |
| Number of dual-polarity pulses in a pulse train | $N_P$ | 1-100 |
| Spacing between consecutive pulse trains | $\Delta_T$ | 0.3-100 ms |
| Number of pulse trains in a burst | $N_T$ | 1-100 |
| Length of a burst | | 1-500 msec |
| Energy | | ≤60 J |
| Total time for PFA signal delivery | | ≤10 s |
| Amplitude of optional RF signal | $V_{RF}$ | 10-200 V |
| Frequency of optional RF signal | $f_{RF}$ | 500 kHz |

As seen in Table 1, PFA pulses and RF signal differ, where the voltage amplitude of an optional RF signal is up to 200 V, while the PFA voltage amplitudes is above 1000 V.

Figure 3:
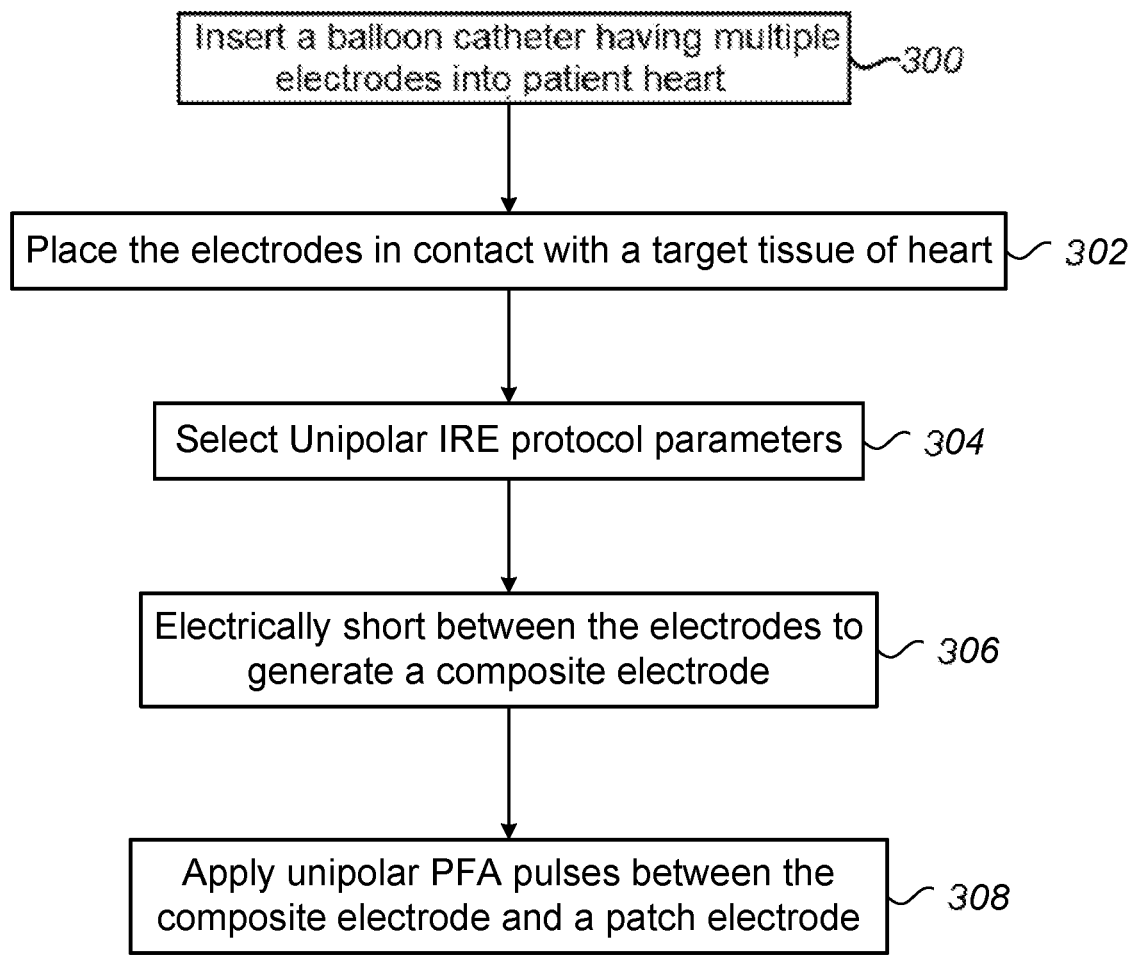
FIG. 3 is a flow chart that schematically illustrates a method for applying unipolar PFA pulses using the system of FIG. 1, in accordance with an embodiment of the present invention.

FIG. 3 is a flow chart that schematically illustrates a method for applying unipolar pulsed-field ablation (PFA) pulses using system 20 of FIG. 1, in accordance with an embodiment of the present invention. The algorithm, according to the presented embodiment, carries out a process that begins at a catheter insertion step 300, with physician 30 inserting, into patient heart 26, balloon 40 which has multiple electrodes 50 disposed on the balloon in a radial geometry. At an electrode placing step 302, electrodes 50 are placed in contact with the target tissue (e.g., at ostium 51) of heart 26, as described in in FIGS. 1 and 2 above.

At IRE protocol selection step 304, physician 30 selects a protocol having parameters suitable for pulsed unipolar PFA, such as provided in Table 1.

At electrodes shorting step 306, processor 41 controls switching assembly 48 to electrically short between electrodes 50 to create composite electrode 250, as described in in FIGS. 1 and 2.

Finally, at a unipolar PFA ablation step 308, processor 41 controls RF generator 38 to apply unipolar PFA pulses between composite electrode 250 placed in contact with the target tissue, and patch electrode 66 as described in FIG. 2 above.

Although the embodiments described herein mainly address cardiac applications, the methods and systems described herein can also be used in other medical applications, such as in lung and liver cancers.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A pulsed field ablation (PFA) system, comprising:
multiple electrodes coupled to a distal end of a catheter configured for insertion into an organ of a patient;
a body-surface electrode configured to be attached to a skin of the patient;
a PFA generator, which is configured to be electrically connected to the multiple electrodes of the catheter and to the body-surface electrode, and to generate Direct-Current (DC) PFA pulses, wherein the DC PFA pulses are configured for ablating target tissue of the organ; and
a processor, which is configured to control the PFA generator to apply the DC PFA pulses between the multiple electrodes and the body-surface electrode while the multiple electrodes are placed in contact with target tissue of the organ and the body-surface electrode is in contact with the skin of the patient; and
a switching assembly connected between a proximal end of the catheter and the PRA generator, wherein the switching assembly is only configured for connecting all the multiple electrodes to one lead of a PFA generator output prior to ablating the target tissue with the DC PFA pulses, and wherein the connecting all the multiple electrodes to one lead is based on electrically shorting the multiple electrodes.

2. The PFA system according to claim 1, wherein electrically shorting the multiple electrodes is configured to form a single composite electrode configured for simultaneously ablating an entire circumference of an ostium of a pulmonary vein (PV).

3. The PFA system according to claim 1, wherein the catheter comprises an expandable frame coupled to the distal end of the catheter, and wherein the multiple electrodes are disposed on the expandable frame.

4. The PFA system according to claim 1, wherein the PFA generator is configured to generate the DC PFA pulses with voltage polarities that alternate from pulse to pulse.

5. The PFA system according to claim 1, wherein the PFA generator is configured to generate the DC PFA pulses in multiple bursts separated by pause intervals.

6. The PFA system according to claim 1, wherein the DC PFA pulses are dual-polarity DC PFA pulses.

7. The PFA system according to claim 1, wherein the processor is configured to at least one of capture signals and track respective locations of each of the multiple electrodes inside a heart based on the switching assembly disconnecting the imposed electrical short.

8. A pulsed field ablation (PFA) method, comprising:
inserting into an organ of a patient multiple electrodes coupled to a distal end of a catheter;
attaching a body-surface electrode to a skin of the patient;
applying Direct-Current (DC) PFA pulses configured for ablating target tissue of the organ between the multiple electrodes of the catheter and the body-surface electrode while the multiple electrodes are placed in contact with target tissue of the organ and the body-surface electrode is in contact with the skin of the patient; and
connecting a switching assembly between a proximal end of the catheter and the generator, wherein the switching assembly is only configured for toggling between connecting and disconnecting all the multiple electrodes to one lead of a PEA generator;
operating the switching assembly to electrically short the multiple electrodes prior to applying the DC PFA pulses for delivering a unipolar DC PFA ablation signal for ablating the target tissue.

9. The PFA method according to claim 8, wherein electrically shorting the multiple electrodes is configured to form a single composite electrode configured for simultaneously ablating an entire circumference of an ostium of a pulmonary vein (PV).

10. The PFA method according to claim 8, wherein applying the DC PFA pulses comprises applying the DC PFA pulses with voltage polarities that alternate from pulse to pulse.

11. The PFA method according to claim 8, wherein applying the DC PFA pulses comprises applying the DC PFA pulses in multiple bursts separated by pause intervals.

12. The PFA method according to claim 8, wherein the DC PFA pulses are dual-polarity DC PFA pulses.

13. The PFA method according to claim 8, comprising at least one of capturing signals and tracking respective locations of each of the multiple electrodes inside a heart based on the switching assembly disconnecting the imposed electrical short.

* * * * *